United States Patent [19]

Shannon et al.

[11] 3,947,564

[45] Mar. 30, 1976

[54] RADIOACTIVE DETERMINATION OF SERUM THYROXINE

[75] Inventors: Charles F. Shannon, Concord; Robert V. Dahlstrom, San Rafael, both of Calif.

[73] Assignee: Bio-Rad Laboratories, Richmond, Calif.

[22] Filed: May 29, 1973

[21] Appl. No.: 364,564

[52] U.S. Cl.................... 424/1; 23/230 B; 250/303
[51] Int. Cl.².................... G01N 33/00; G01T 1/16
[58] Field of Search.......... 424/1, 79, 357; 23/230 B

[56] References Cited
UNITED STATES PATENTS

| | | | |
|---|---|---|---|
| 3,414,383 | 12/1968 | Murphy | 424/1 X |
| 3,451,777 | 8/1965 | DiGiulio | 424/79 X |
| 3,555,001 | 1/1971 | Wallis et al. | 424/79 X |
| 3,659,104 | 4/1972 | Gross et al. | 424/1 X |
| 3,666,854 | 5/1972 | Eisentraut | 424/357 X |
| 3,714,344 | 1/1973 | Brown | 424/1 |
| 3,776,698 | 12/1973 | Eisentraut | 424/357 X |

*Primary Examiner*—Benjamin R. Padgett
*Assistant Examiner*—Christine M. Nucker
*Attorney, Agent, or Firm*—Townsend and Townsend

[57] ABSTRACT

A method for determining serum thyroxine (T-4) in which the T-4 is first separated from the serum by adsorption onto a montmorillonite clay and then competitively bound by exogenous thyroxine binding globulin in the presence of a known amount of radioactive T-4. The competitively bound serum T-4 and radioactive T-4 is separated from the unbound serum T-4 and radioactive T-4 by passage through an ion exchange resin column. The serum T-4 concentration is determined by measuring the amount of bound radioactive T-4 and referring to a standard curve.

10 Claims, No Drawings

RADIOACTIVE DETERMINATION OF SERUM THYROXINE

This invention relates to the determination of serum thyroxine (T-4). More particularly, it relates to the determination of serum thyroxine utilizing the principle of competitive protein binding and in which measurements are made on the radioactivity of a known amount of radioactive T-4 added to the solution in which the competitive binding occurs.

A summary of the prior art techniques which have been used for measuring serum thyroxine appears in recently issued U.S. Pat. No. 3,659,104. The present invention is an improvement upon such prior art. Thus, the present method avoids the alcohol precipitation/extraction required in the procedure of Murphy, et al. referred to in said patent. As a result, patient serum to be analyzed in accordance with the present methods can be stored for relatively extended periods. For example, the serum sample may be stored under refrigeration (3°-8° C.) for 1 week or longer without alteration of the test results. The present method improves upon said U.S. Pat. No. 3,659,104 itself by providing a simplified procedure of less steps and which can be executed much more rapidly.

SUMMARY OF THE INVENTION

A serum sample which is to be analyzed for its T-4 content is initially treated to separate the thyroxine from its serum proteins. The present invention provides a novel step for accomplishing this separation. The thyroxine is adsorbed onto a montmorillonite clay in acid solution. The clay containing the adsorbed thyroxine is then separated from the serum as by centrifuging. The thyroxine is thereafter eluted from the clay by contact with an alkaline solution. In the preferred embodiment elution of the thyroxine from the clay is executed concurrently with a competitive binding step by which the serum thyroxine competes with a known amount of radioactive T-4 for the available binding sites on thyroxine binding material. Bound serum thyroxine and radioactive T-4 is separated from unbound T-4 and radioactive T-4. In the preferred embodiment this is executed by flowing the equilibrated competitive binding mixture through a column containing ion exchange resin in which column dimensions and resin type are adapted to retain unbound T-4 and radioactive T-4 while permitting bound T-4 and radioactive T-4 to flow therethrough. In this regard, the present invention provides another novel step in the use of ion exchange resins for such a separation. The amount of radioactive T-4 bound by the thyroxine binding material is then measured. By referring to a standard curve the serum thyroxine content of the sample may then be obtained.

DESCRIPTION OF THE PREFERRED EMBODIMENTS

Step 1: Separation of Thyroxine From Serum 0.1 Ml. of serum and 3.0 ml. of .025 N HCl and 10 mg. of Bentonite was placed in a 13 × 100 mm. test tube. The Bentonite is a colloidal, native hydrated aluminum silicate. The material is allowed to stand for at least 90 seconds and thereafter mixed vigorously to suspend the particles. Thereafter, the clay is separated from the supernatant, for example, by centrifuging. During this step the acidic solution causes the thyroxine to dissociate from its serum proteins and to be adsorbed by the Bentonite.

The amount of clay utilized is relatively critical. Approximately 10 mg. of clay should be used for each 0.0–0.3 ml. of serum and preferably about 10 mg. of Bentonite should be used for each 0.1 ml. of serum.

Step 2: Elution of T-4 From the Clay and Competitive Binding

To the test tube containing the Bentonite and adsorbed T-4 is added 3 ml. of 0.025 M sodium carbonate ($Na_2CO_3$). The contents of the tube are mixed well to resuspend the clay particles. One and one-half ml. of 0.05 M barbital buffer which contains 0.05 M sodium 5,5-diethyl barbiturate adjusted to pH 7.7 (with HCl), 0.01% sodium azide, and pooled human serum diluted 1–40 to 1.70 by the buffer, and $0.1\mu Ci$ of T-4 labeled with a radioactive isotope (of 1–125 thyroxine) are added to the test tube and mixed well. (The final mixture has a pH of 8.6). The contents of the test tube are allowed to stand for at least 15 minutes at ambient temperature. The clay is then removed as by centrifugation. During this step the alkaline solution causes the thyroxine to be eluted from the clay. The eluted thyroxine then competes with the radioactive T-4 for the available binding sites on the added thyroxine binding material which in this case is (thyroxine binding globulin from) the pooled human serum.

Step 3: Separation of Bound and Unbound T-4

An ion exchange resin column in which the resin has a bed height of about 2.0 cm. and a diameter of about 0.295 inches is selected. The resin in the column is 50–100 mesh styrene-divinyl benzene anion exchange resin of 8% cross linkage (available from Bio-Rad Laboratories, Richmond, California under the designation AG1-X8). Alternatively, the ion exchange resin is a 50–100 mesh ion retardation resin containing paired anion and cation exchange sites. (Available from Bio-Rad Laboratories, Richmond, California, under the designation AG11A8). Column dimensions and resin type and mesh are critical in order to achieve this separation using ion exchange resins.

The contents of the test tube at the completion of Step 2 are poured and flowed through the column of resin and the eluate collected. During this step the free thyroxine and free radioactive T-4 are retained by the resin while the T-4 and radioactive T-4 bound by the exogenous human thyroxine binding globulin from the pooled serum passes through and is collected in the eluate. The radioactivity in the eluate or on the column may be counted. Preferably the radioactivity of the eluate is counted.

Step 4: Serum Thyroxine Determined

The thyroxine content of unknown patient serum can be determined by comparing the radioactivity count obtained in Step 3 with a standard curve developed using the steps of this process in connection with known or standard serum samples.

If it is desired, an Estimated Thyroxine Index of a serum sample can be determined in accordance with the present procedure. After the separation of T-4 from the serum proteins has been executed in accordance with Step 1, a $5\mu l$ aliquot of the same serum sample is added after the other materials of Step 2 have been added and then mixed well (and allowed to stand 15 minutes). This additional amount of the unknown serum provides additional binding sites to receive unbound radioactive T-4 during Step 2. Measuring the amount of bound or unbound radioactive T-4 as outlined above is thus a measure of the unknown serum T-4 concentration and the binding capacity of the serum. Values are computed from the radioactivity count obtained at the conclusion of Step 4 in accordance with the following equation:

$$ETI = \frac{cpmsc}{cpm_x}$$

ETI = Estimated Thyroxine Index
$cpm_x$ = counts per minute of patient's serum
$cpmsc$ = counts per minute of standard control serum $$c = \frac{\text{known value of control serum at } T\text{-4 iodine}}{4.2}$$

The use of montmorillonite clay to separate T-4 from serum proteins is one of the novel features of the present process. The montmorillonite group of clays such as the Bentonite member is substantially more efficient in the adsorption of thyroxine than other adsorbents that might be selected. To illustrate the efficiency of the montmorillonites, the following comparison was made with results tabulated in Table I.

TABLE I

COMPARISON OF SEVERAL ADSORBENTS FOR THE SEPARATION OF THYROXINE FROM SERUM

| Adsorbent | % Thyroxine Adsorbed |
| --- | --- |
| Florisil | 73 |
| Talc | 85 |
| Britesorb | 11 |
| Hydroxylapatite | 33 |
| Zirconiumphosphate | 12 |
| Kaolin | 30 |
| Bentonite | 97 |

50 Mg. of adsorbent in 3 ml. of 0.025 N HCl used as the adsorbent. To this add 0.1 ml. of control serum spiked with radioactive thyroxine. Mix thoroughly and incubate 10 minutes at 23° C. Centrifuge 5 minutes, decant supernatant and count radioactivity in the supernatant. The decrease in counts of the supernatant is a direct measure of the thyroxine adsorbed to the material.

As previously indicated, the amount of clay used relative to the serum sample is most important. In order to obtain a good elution recovery of the thyroxine from the clay, the proportion of serum to clay previously indicated should be followed. The following illustrates the losses on recovery where the proper ratio of serum to clay is not utilized.

TABLE II

RECOVERY OF THYROXINE FROM BENTONITE

| Bentonite Conc | % Thyroxine Recovered |
| --- | --- |
| 50 mg. | 48 |
| 25 mg. | 60 |
| 10 mg. | 84 |

Bentonite was suspended in 3 ml. 0.025 N HCl. To this 0.1 ml. control serum containing a known amount of radioactive T-4 was added. The suspension was mixed, incubated for 10 minutes and centrifuged. The supernatant was decanted and counted to determine percent thyroxine adsorbed. The clay was resuspended in 0.025 N $Na_2CO_3$, mixed and centrifuged. Under alkaline conditions the thyroxine is eluted from the Bentonite. The supernatant is counted and the total percent recovered is calculated by dividing the total counts recovered by the total counts of radioactive T-4 added.

We claim:

1. In the determination of thyroxine ("T-4") in blood serum including the steps of separating T-4 from serum, competitively binding a portion of said separated T-4 with thyroxine binding material in the presence of a known amount of radioactive T-4, separating radioactive T-4 bound by said thyroxine binding material from unbound radioactive T-4, and measuring the amount of bound or unbound radioactive T-4 whereby serum T-4 concentration may be determined therefrom, the improvement comprising: executing said step of separating T-4 from serum by contacting the serum with an effective amount of a montmorillonite clay under acidic conditions to adsorb the serum T-4 thereon, separating said montmorillonite clay from said serum, and then separating adsorbed T-4 from said clay, by introducing said clay into an alkaline solution, whereby said T-4 is freed from said clay.

2. In the determination of T-4 in blood serum in accordance with claim 1 the improvement wherein said montmorillonite is a bentonite clay.

3. In the determination of T-4 in blood serum in accordance with claim 2 wherein said bentonite is contacted with said serum to adsorb its T-4 content thereon in an amount of about 10 mg. bentonite for each 0–0.3 ml. of serum.

4. In the determination of T-4 in blood serum in accordance with claim 3 wherein said bentonite is contacted with said serum in an amount of about 10 mg. of Bentonite for 0.1 ml. of serum.

5. A method for the determination of thyroxine ("T-4") in blood serum comprising: separating T-4 from serum by adsorbing the T-4 onto a montmorillonite clay in acidic, wherein said clay is employed in the amount of about 10 mg. per 0.0–0.3 ml. of serum, separating the clay with the adsorbed T-4 from the remainder of the serum, adding said clay with adsorbed T-4 to an alkaline solution and then adding a thyroxine binding material containing thyroxine binding material and a preselected amount of radioactive T-4, the T-4 eluting from said clay into said alkaline solution and competing with said radioactive T-4 for the binding sites on said thyroxine binding material, separating the thyroxine binding material with serum T-4 and radioactive T-4 bound thereto from unbound serum T-4 and unbound radioactive T-4, and measuring the amount of bound or unbound radioactive T-4 whereby serum T-4 concentration may be determined therefrom.

6. A method in accordance with claim 5 wherein said montmorillonite clay is a bentonite clay and the amount of radioactive T-4 bound to the thyroxine binding material is measured to determine serum T-4 concentration.

7. A method in accordance with claim 5 wherein separation of T-4 and radioactive T-4 bound by thyroxine binding material from unbound T-4 and radioactive T-4 is executed by passing the combination thereof through a column containing ion exchange resin in which column dimensions and resin type are adapted to retain unbound T-4 and radioactive T-4 while permitting bound T-4 and radioactive T-4 to flow therethrough.

8. A method in accordance with claim 7 wherein said resin is a 50–100 mesh ion retardation resin containing paired anion and cation exchange sites.

9. The method in accordance with claim 7 wherein the resin in said column has a bed height of about 2.0 cm. and a diameter of about 0.295 inches.

10. A method for the determination of thyroxine ("T-4") in blood serum comprising: separating T-4 from serum by adsorbing the T-4 onto bentonite clay in acidic solution, wherein about 10 mg. of said clay is employed for from 0.0–0.3 ml. of serum, separating the clay with the adsorbed T-4 from the remainder of the serum, adding said clay with adsorbed T-4 to an alkaline solution and then adding a thyroxine binding material containing thyroxine binding material in a preselected amount of radioactive T-4, the T-4 eluting from said clay into said alkaline solution and competing with said radioactive T-4 for the binding sites on said thyroxine binding material, separating the thyroxine binding materials, serum T-4 and radioactive T-4 bound thereto from unbound serum T-4 and unbound radioactive T-4 by passing the combination thereof through a column of anion exchange resin which is a 50–100 mesh styrene-divinyl benzene anion exchange resin of 8% cross linkage, of dimensions to retain unbound T-4 and radioactive T-4 while permitting bound T-4 and radioactive T-4 to flow therethrough, and measuring the amount of bound or unbound radioactive T-4, whereby serum T-4 concentration may be determined therefrom.

\* \* \* \* \*